United States Patent
Qi et al.

(10) Patent No.: US 10,543,296 B2
(45) Date of Patent: Jan. 28, 2020

(54) ABSORBABLE IRON-BASED ALLOY MEDICAL INSTRUMENT IMPLANT AND MANUFACTURING METHOD

(71) Applicant: Lifetech Scientific (Shenzhen) Co., Ltd., Shenzhen (CN)

(72) Inventors: Haiping Qi, Shenzhen (CN); Ziqiang Liu, Shenzhen (CN); Li Qin, Shenzhen (CN); Deyuan Zhang, Shenzhen (CN); Wenjiao Lin, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 15/767,610

(22) PCT Filed: Jun. 7, 2016

(86) PCT No.: PCT/CN2016/085046
§ 371 (c)(1),
(2) Date: Apr. 11, 2018

(87) PCT Pub. No.: WO2017/063372
PCT Pub. Date: Apr. 20, 2017

(65) Prior Publication Data
US 2018/0303971 A1 Oct. 25, 2018

(30) Foreign Application Priority Data
Oct. 14, 2015 (CN) .......................... 2015 1 0663121

(51) Int. Cl.
*A61L 27/04* (2006.01)
*A61L 27/54* (2006.01)
*A61L 27/58* (2006.01)
*A61L 27/18* (2006.01)
*A61L 27/40* (2006.01)
*A61L 31/12* (2006.01)

(52) U.S. Cl.
CPC ............. *A61L 27/042* (2013.01); *A61L 27/18* (2013.01); *A61L 27/40* (2013.01); *A61L 27/54* (2013.01); *A61L 27/58* (2013.01); *A61L 31/12* (2013.01)

(58) Field of Classification Search
None
See application file for complete search history.

(56) References Cited

U.S. PATENT DOCUMENTS

2007/0250155 A1* 10/2007 Simpson .................. A61F 2/91
623/1.16
2014/0206630 A1* 7/2014 Messersmith ............ C08J 7/065
514/25

FOREIGN PATENT DOCUMENTS

| CN | 102228721 | * | 11/2011 |
|---|---|---|---|
| CN | 104195535 | A | 12/2014 |
| CN | 104587534 | A | 5/2015 |
| CN | 104784750 | A | 7/2015 |

OTHER PUBLICATIONS

English Translation of CN 102228721 (Specification only), 2011.*
Office Action dated Feb. 3, 2019 for corresponding China Application No. 201510663121.9.

* cited by examiner

*Primary Examiner* — Bong-Sook Baek
(74) *Attorney, Agent, or Firm* — Raymond Sun

(57) ABSTRACT

Absorbable iron-based alloy implanted medical device and manufacturing method thereof. The iron-based alloy implanted medical device comprises an iron-based alloy substrate (11), a degradable polymer layer (13) disposed on a surface of the iron-based alloy substrate (11), and a tannic acid chemical conversion film (12) disposed on a surface of the iron-based alloy substrate (11). After the medical device is implanted into a body, the tannic acid chemical conversion film (12) is configured to protect the iron-based alloy substrate (11) coated thereby from being in contact with a body fluid, thereby ensuring that the device meets a clinical mechanical property requirement in the early stage of implantation. Furthermore, the iron-based alloy implanted medical device has a decreased size, and produces a decreased amount of a corrosive product after being implanted, facilitating faster absorption or elimination of the corrosive product.

15 Claims, 1 Drawing Sheet

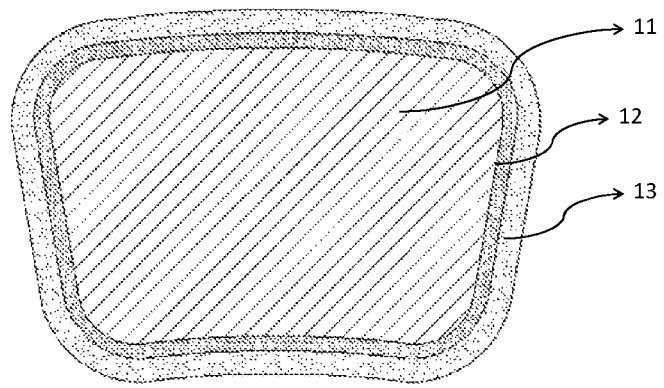

ABSORBABLE IRON-BASED ALLOY MEDICAL INSTRUMENT IMPLANT AND MANUFACTURING METHOD

TECHNICAL FIELD

The present application belongs to the field of absorbable implanted medical devices, and more particularly relates to an absorbable iron-based alloy implanted medical device and a manufacturing method thereof.

BACKGROUND ART

At present, matrix materials for an absorbable implanted medical device mainly include polymers, a magnesium-based alloy and an iron-based alloy. The most frequently applied polymer is polylactic acid, which can be completely degraded and absorbed, with degradation products of carbon dioxide and water, but its mechanical property is poor. The size of the polymer-based device should be larger than the metal-based device so that the polymer-based device has the same mechanical property as the metal-based device, which limits application of the polymer-based device. The magnesium-based alloy and the iron-based alloy have advantages of ease in processing and molding, and high mechanical strength. However, as the magnesium-based alloy corrodes too quickly in a human body, it is necessary to enlarge the size of a magnesium-based alloy device to obtain the mechanical property in the early stage of implantation, and this also limits the application of the magnesium-based alloy device.

In terms of clinical application, when the absorbable implanted medical device fulfills its expected use, after a diseased portion is cured and is recovered to its normal shape and function (cured), on the premise of not causing a new biological compatibility problem, the less time needed for the device to be completely degraded and absorbed by an organ the better. According to different portions to which the device is clinically applied, the recovery period is generally considered as 1 to 6 months, and within this period of time, the device is required to keep a structural integrity and have a sufficient mechanical property. When used as an implanted medical device matrix material, the iron-based alloy has a good biological compatibility, and iron ions contribute to inhibiting smooth muscles and promoting growth of endothelial cells, but due to the slow corrosion of the iron-based alloy in the body, the iron-based alloy device would not be corroded completely until a long time after the diseased portion is cured; and therefore, it is necessary to accelerate corrosion to shorten the corrosion cycle of the iron-based alloy.

A research has shown that if the surface of the iron-based alloy is coated with a degradable polyester coating, its corrosion speed would be increased. Degradation of the degradable polyester coating in the body would lower the pH value of a local microenvironment near a device implantation position, thereby forming a local micro acidic environment where the iron-based alloy is corroded faster to generate iron salt and/or iron oxides and/or iron hydroxides serving as corrosion products.

For the iron-based alloy device of a predetermined specification, the corrosion speed of the iron-based alloy and whether the iron-based alloy is finally completely corroded or not are determined according to the amount of the degradable polyester coating and the type and the nature of degradable polyester. Under conditions that the type and the nature of the degradable polyester have been selected and the amount of the degradable polyester is sufficient to completely corrode an iron-based alloy substrate, extremely high corrosion speed or local severe corrosion of the iron-based alloy would affect the structural integrity and the mechanical property of the iron-based alloy device in the early stage of implantation (1 to 6 months, namely the above-mentioned recovery period), thereby it is difficult for the device to meet a requirement for clinical application. These defects are specifically as follows: (1) a degradation product of the degradable polyester coating is acidic, and there are small molecular residues with a higher degradation speed in degradable polyester (for example, the standard monomer residue amount of the polylactic acid is less than 2%), that will result in faster corrosion of the iron-based substrate in the early stage of implantation, for example, after the device is implanted into a coronary artery for about to 7 days, excessively fast corrosion and accumulation of the corrosion products cause incomplete endothelialization of the inner surface of the device, which increases a risk of acute thrombosis and subacute thrombosis; and (2) the heterogeneity of degradable polyester degradation easily leads to non-uniform corrosion of the iron-based alloy substrate, and local fast corrosion possibly results in breakage, which leads to a fact that it is hard for the iron-based alloy substrate to meet requirements on a structural integrity and a mechanical property in the early stage. Although the excessively fast corrosion of the iron-based alloy device in the early stage of implantation can be prevented by reducing the amount of the degradable polyester coating, the corrosion cycle of the iron-based alloy device would be prolonged. Therefore, for the iron-based alloy device including degradable polyester, under the conditions that the type and the nature of the degradable polyester and a ratio of the amount of degradable polyester to the iron-based alloy are determined, it is necessary to seek a way to reduce the early corrosion speed of the iron-based substrate in the acidic environment which is generated by the degradable polyester to guarantee the mechanical property of the device in the early stage of implantation.

SUMMARY OF THE INVENTION

To address the shortcomings in the prior art, the object of the present application is to provide an absorbable iron-based alloy implanted medical device. After being implanted into a body, the absorbable iron-based alloy implanted medical device is corroded slowly or is totally not corroded within 1 to 6 months, and can meet a clinical requirement on a mechanical property of the device in the early stage of implantation.

An absorbable iron-based alloy implanted medical device is provided, including: an iron-based alloy substrate, a degradable polymer layer disposed on the surface of the iron-based alloy substrate, and a tannic acid chemical conversion film disposed on the surface of the iron-based alloy substrate.

The tannic acid chemical conversion film may cover all surfaces of the iron-based alloy substrate and may also cover part of the surfaces of the iron-based alloy substrate. When the tannic acid chemical conversion film covers all the surfaces of the iron-based alloy substrate, the degradable polymer layer covers at least part of surfaces of the tannic acid chemical conversion film. When the tannic acid chemical conversion film does not cover all the surfaces of the iron-based alloy substrate, the degradable polymer layer may only covers at least part of the surfaces of the tannic acid chemical conversion film, or the degradable polymer layer and the tannic acid chemical conversion film cover different surfaces of the iron-based alloy substrate in a staggering manner, or the degradable polymer layer covers at least part of the surfaces of the tannic acid chemical conversion film and at least part of non-covered regions. The iron-based alloy substrate may be selected from an iron-based alloy or pure iron with a carbon content less than or equal to 2.11 wt. %, such as a product obtained by performing nitriding and/or carburization on the pure iron.

The tannic acid chemical conversion film is a product generated by reaction of tannic acid and the iron-based alloy substrate.

The degradable polymer is selected from degradable polyester and/or degradable polyanhydride. The degradable polyester is selected from any one of polylactic acid, polyglycolic acid, poly(lactic acid-glycolic acid), polycaprolactone, polyhydroxyalkanoate. polyacrylate, poly(ethylene succinate), poly(β-hydroxybutyrate) and polyethylene glycol adipate, or is selected from a physical blend of at least two of the polylactic acid, the polyglycolic acid, the poly(ethylene succinate), the poly(β-hydroxybutyrate), the polycaprolactone, the polyethylene glycol adipate, a polylactic acid-glycolic acid copolymer and a polyhydroxybutyrate-pentanoate copolymer, or is selected from any one of copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycolic acid copolymer and the polyhydroxybutyrate-pentanoate copolymer. The degradable polyanhydride is selected from at least one of poly 1,3-bis(p-carboxyphenoxy)propane-sebacic acid. poly(erucic acid dimer-sebacic acid) or poly(fumaric acid-sebacic acid), or the degradable polymer is a copolymer formed by copolymerizing at least two of monomers forming the degradable polyester and the degradable polyanhydride.

An active drug is mixed into the degradable polymer, such as an anti-intimal hyperplasia drug for treating vascular restenosis, an anticoagulant, an anti-platelet adhesion drug, an anti-infective drug, an antibacterial drug or an anti-tumor drug.

The implanted medical device is a heart implant such as an occluder, a blood vessel implant such as a stent a gynecological implant, an andrological implant, a respiratory implant or an orthopedic implant.

The present application further provides a manufacturing method for an absorbable iron-based alloy implanted medical device, including the steps of:

(1) soaking an iron-based alloy substrate in a tannic acid solution for reaction, thus forming a tannic acid chemical conversion film;
(2) preparing a degradable polymer layer on the surface of the absorbable iron-based alloy implanted medical device prepared in the above-mentioned step;

wherein the concentration of the tannic acid solution ranges from 2 to 10 g/L, a reaction temperature is 15 to 45° C. and reaction time is 5 to 60 min.

The manufacturing method further includes the step of sealing holes of the substrate with the tannic acid chemical conversion film formed on the surface by using boiling water for 20 to 30 min.

Compared with the prior art, the absorbable iron-based alloy implanted medical device provided by the present application includes the tannic acid chemical conversion film. After the device is implanted into a body, the tannic acid chemical conversion film protects the iron-based alloy substrate covered thereby from being in contact with body fluid, so that the iron substrate is not corroded. After the tannic acid chemical conversion film is nearly completely consumed, the iron-based alloy substrate protected thereby is corroded quickly, thus ensuring that the device meets a clinical mechanical property requirement in the early stage of implantation. In addition, the absorbable iron-based alloy implanted medical device has a decreased design size, and produces a decreased amount of corrosion products after being implanted, facilitating faster absorption or elimination of the corrosion products.

BRIEF DESCRIPTION OF THE DRAWINGS

FIG. 1 is a sectional schematic diagram of an absorbable implanted medical device of the present application along its lengthwise direction. As shown in the FIGURE, 11 is for an iron-based alloy substrate. 12 is for a tannic acid chemical conversion film, and 13 is for a polymer layer.

DETAILED DESCRIPTION OF THE INVENTION

In order to facilitate understanding of the present application, a more complete description is made to the present application in connection with the accompanying drawing as follows. A preferred embodiment is as shown in the FIGURE. However, the present application may be implemented in many different forms, and not limited to the embodiments described herein. On the contrary, the embodiments provided are intended to enable the disclosed subject matter of the present application to be more thorough and comprehensive.

Unless otherwise defined, all technical and scientific terms used in the text have the same meanings of general understandings of persons skilled in the art of the present application. Terms used in the description of the present application in the text are intended to describe the specific embodiments, but not to limit the present application.

There are various positional relationships between a tannic acid chemical conversion film and an iron-based alloy substrate, and there are many kinds of positional relationships among the degradable polymer layer and the tannic acid chemical conversion film and the iron-based alloy substrate. As an implementation mode, as shown in FIG. 1, the tannic acid chemical conversion film 12 directly completely covers the surface of the iron-based alloy substrate 11, and the degradable polymer layer 13 also directly completely covers the tannic acid chemical conversion film 12.

The main idea of the present application is that the tannic acid chemical conversion film is disposed on the surface of the existing absorbable iron-based alloy implanted medical device, and the tannic acid chemical conversion film is configured to prevent the iron-based alloy substrate from being in contact with an acidic environment, thereby controllably delaying a time point that the iron-based alloy substrate starts to be corroded, achieving an effect that the iron-based alloy substrate is not corroded in the early stage of implantation (1 to 6 months), and ensuring that the absorbable iron-based alloy implanted device has a structural integrity in the early stage and a sufficient mechanical property without prolonging the corrosion cycle of the iron-based alloy substrate As the tannic acid chemical conversion film may delay the time point that the iron-based alloy substrate starts to be corroded, within the protection period of the tannic acid chemical conversion film, the mechanical property of the iron-based alloy substrate basically cannot be changed. Therefore, the absorbable iron-based alloy implanted medical device only needs to ensure that the initial mechanical property before implantation reaches a lower limit of a clinical requirement in the early stage of implantation, and it is unnecessary that the absorbable iron-based alloy implanted medical device still have a relatively high mechanical property beyond the recovery period. Thus, compared with the prior art, the absorbable iron-based alloy implanted medical device of the present application has a decreased design size, and the amount of iron is correspondingly lowered, thereby fulfilling the aim of reducing iron corrosion products.

Specifically, a reaction of the tannic acid chemical conversion film and a hydrogen ion formed by degradation of the degradable polymer is slower than that of an iron-based alloy and the hydrogen ion formed by the degradation of the degradable polymer. Furthermore, the tannic acid chemical conversion film is of a polyphenol hydroxyl structure, and a product obtained by reaction of the tannic acid chemical conversion film and an acid has a reducing property, and combination of the tannic acid chemical conversion film with internal proteins, alkaloid and polysaccharide may further slow down corrosion of the iron-based alloy substrate in the acidic environment. In addition, under the action of an internal enzyme, tannic acid serving as a reaction product of the tannic acid chemical conversion film and the acid is degraded into carbon dioxide and water which have no impact on a human body. Therefore, the tannic acid chemical conversion film formed on the surface of the iron-based alloy substrate of the implanted medical device may effectively delay early corrosion in the initial stage of implantation of the medical device.

As the tannic acid chemical conversion film may achieve a corrosion inhibition effect on the iron-based alloy substrate, and thickness increase would prolong the corrosion inhibition time, in the present application, the thickness of the tannic acid chemical conversion film can be adjusted by adjusting a reaction condition of the iron-based alloy substrate and the tannic acid, such as reaction time, so that the starting time of corrosion of the iron-based alloy implanted medical device can be adjusted; and by adjusting of the type and the thickness (mass) of the polymer layer, the corrosion rate of the iron-based alloy substrate also can be adjusted.

The absorbable iron-based alloy implanted medical device of the present application may be a blood vessel stent, an orthopedic implant, a gynecological implant, an andrological implant, a respiratory implant or an orthopedic implant. By taking an iron-based alloy coronary artery stent as an example, a detailed description is further made to the present application in connection with specific embodiments as follows, but not intended to limit the scope of protection of the present application.

It should be noted that animal experiments in all embodiments as follows show that under the action of the tannic acid chemical conversion film, the iron-based alloy stent is nearly not corroded within 1 to 6 months of the early stage of implantation. The in vivo corrosion state of the iron-based alloy stent and whether a mechanical property requirement in the early stage is met or not are expressed by main measures of executing euthanasia to animals in which the stents are placed at different observation time points, such as 3 months 6 months, 12 months, 2 years and 3 years, and then removing each stent and a tissue of a portion where the stent is placed and conducting a radial supporting strength and mass loss test on the stent and a blood vessel segment where the stent is placed.

For clinical supporting strength, the diastolic pressure (low pressure) and the systolic pressure (high pressure) of a coronary vessel of a normal person are 60 to 120 mmHg, but the systolic pressure of a hypertension patient is up to 175 mmHg, namely 23.3 kPa. In case of coronary artery spasm, the systolic pressure of the vessel is 400 mmHg, namely 55 kPa. A psychological stress state, a cold stimulation, a strenuous exercise, coronary atherosclerosis and a local stimulation to the coronary artery due to coronary angiogram as well as one-time heavy smoking or drinking may all induce the coronary artery spasm. Thus, in order to achieve an effective support for the coronary vessel, the stent must at least bear the systolic pressure of 23.3 kPa in case of pulsation of the coronary vessel, and should bear the systolic pressure of 55 kPa in case of vasospasm.

One way of testing the radial supporting strength of the stent is as follows: uniformly applying a radial pressure to the stent through a compression module to compress the stent to generate a uniform deformation. It is defined that the radial pressure intensity applied when the stent deforms by 10 percent in a radial direction (the outer diameter) is the radial strength of the stent. The radial supporting strength test is carried out with a radial supporting strength tester (RX550-100) produced by the MSI company, taking out the stent implanted into the body of the animal and the blood vessel, sucking dry the surface, and then directly carrying out the test, thus obtaining the radial supporting strengths of the stent at different time points after the stent is implanted.

One way of testing the weight loss is as follows: implanting an iron-based alloy stent (with a degradable polymer) including an iron-based alloy substrate (which is a naked stent without the degradable polymer) with the mass of M0 into an abdominal aorta of a rabbit, capturing the iron-based alloy stent implanted into the body of the animal and a tissue where the stent is placed at a preset observation time point, then soaking the tissue and the stent in 1 mol/L sodium hydroxide solution to digest the tissue, taking the iron-based alloy stent or a fragment thereof out of the solution, putting it into a solution at a certain concentration (such as a tartaric acid solution at the concentration of 3%, and/or an organic solution) for ultrasonic treatment to enable a corrosion product on its surface and the polymer layer to completely fall into or be dissolved in the solution, taking the residual non-corroded iron-based alloy stent or fragment thereof out of the solution, drying and weighing it, and recording the mass as Mt. A mass loss rate W is represented by a percentage of a difference value of the weight loss of a corroded and cleaned stent lever to the weight of the iron-based substrate, as shown in Formula 1:

$$W = (M_t - M_0)/M_0 \times 100\% \quad (1)$$

W represents the mass loss rate $M_t$ represents the mass of the residual iron-based alloy stent substrate after corrosion $M_0$ represents the initial mass of the iron-based alloy stent substrate wherein when the mass loss rate W of the iron-based alloy substrate is less than 5%, it is defined that no corrosion occurs; and when the mass loss rate W of the iron-based alloy substrate is greater than or equal to 90%, it is defined that complete corrosion occurs.

The design target of the iron-based alloy stent provided by each embodiment as follows is to meet the following clinical requirements: after being implanted, the iron-based alloy stent provides effective support for 3 months: after 3 months of implantation, the radial supporting strength is higher than or equal to 55 kPa; and the corrosion cycle is longer than 6 months but shorter than or equal to 24 months.

The definition of the stent of the specification 30008 in each embodiment is as follows: after the stent is expanded under the action of a nominal expansion pressure of 8 atm, the nominal diameter is 3 mm, and the nominal length is 8 mm.

It should be noted that in each embodiment as follows, a normal fluctuation of the performance of a stent product within a designed allowable range, an individual difference of the animal, an insufficient density of designed sampling points, and a system error unavoidably introduced by the test methods, may lead to fluctuations of monitored stent radial strength data and complete corrosion time points within a certain range in an actual test.

Embodiment 1

A polished iron-based alloy coronary artery stent of the specification 30008 was selected, with its original radial strength of 145 kPa and weight of 4.5 mg, and it was soaked in a tannic acid solution with the mass fraction of 4 g/L at a temperature of 20° C. for 20 minutes; then holes were sealed with boiling water for 30 minutes, thus a tannic acid chemical conversion film which covers the surface of an iron-based substrate has a thickness of 0.4 to 0.5 um and has a coverage rate of 95 percent was obtained: after the stent was dehydrated with absolute ethanol, the surface of the stent was subjected to dip coating with a poly-dl-lactic acid-ethyl acetate solution with the molecular weight of 200,000; and after the surface was dried, an absorbable iron-based alloy stent was made. A polylactic acid coating with a thickness of 6 um completely covered the tannic acid chemical conversion film. The stent was implanted into an abdominal aorta of a rabbit and was then taken out after 3 months, and observation found that the stent was corroded to a certain extent and was subjected to full endothelialization, and no early thrombosis and inflammation phenomena were caused. Radial supporting strength test results of the stent and the complete corrosion cycle data monitored in the experiments of the same group of animals are specified in Table 1.

Embodiment 2

A polished iron-based alloy coronary artery stent of the specification 30008 was selected, with its original radial strength of 145 kPa and weight of 4.5 mg, and it was soaked in a tannic acid solution with the mass fraction of 4 g/L at a temperature of 20° C. for 40 minutes: then holes were sealed with boiling water for 30 minutes, thus a tannic acid chemical conversion film which completely covers the surface of an iron-based substrate and has a thickness of 0.8 to 1.0 um was obtained: after the stent was dehydrated with absolute ethanol, the surface of the stent was subjected to spray coating with a poly-dl-lactic acid-ethyl acetate solution with the molecular weight of 200,000; and after the surface was dried, an absorbable iron-based alloy stent was made. A non-continuous polylactic acid coating with a thickness of 8 um was located on the surface of the tannic acid chemical conversion film. The stent was implanted into an abdominal aorta of a rabbit and was then taken out after 3 months, and observation found that the stent was corroded to a certain extent and was subjected to full endothelialization, and no early thrombosis and inflammation phenomena were caused. Radial supporting strength test results of the stent and the complete corrosion cycle data monitored in the experiments of the same group of animals are specified in Table 1.

Embodiment 3

A polished iron-based alloy coronary artery stent of the specification 30008 was selected, with its original radial strength of 145 kPa and weight of 4.5 mg, and it was soaked in a tannic acid solution with the mass fraction of 6 g/L at a temperature of 20° C. for 60 minutes: then holes were sealed with boiling water for 30 minutes, thus a tannic acid chemical conversion film which completely covers the surface of an iron-based substrate and has a thickness of 1.6 to 1.8 um was obtained: after the stent was dehydrated with absolute ethanol, the surface of the stent was subjected to brush coating with a poly-di-lactic acid-ethyl acetate solution with the molecular weight of 200,000; and after the surface was dried, an absorbable iron-based alloy stent was made. A polylactic acid coating with a thickness of 12 um completely covered the tannic acid chemical conversion film. The stent was implanted into an abdominal aorta of a rabbit and was then taken out after 3 months, and observation found that the stent was corroded to a certain extent and was subjected to full endothelialization, and no early thrombosis and inflammation phenomena were caused. Radial supporting strength test results of the stent and the complete corrosion cycle data monitored in the experiments of the same group of animals are specified in Table 1.

Embodiment 4

A polished iron-based alloy coronary artery stent of the specification 30008 was selected, with its original radial strength of 145 kPa and weight of 4.5 mg, and it was soaked in a tannic acid solution with the mass fraction of 6 g/L at a temperature of 20° C. for 60 minutes; then holes were sealed with boiling water for 30 minutes, thus a tannic acid chemical conversion film which completely covers the surface of an iron-based substrate and has a thickness of 1.6 to 1.8 um was obtained; after the stent was dehydrated with absolute ethanol, the surface of the stent was subjected to spray coating with a poly-dl-lactic acid-sirolimus-ethyl acetate solution with the molecular weight of 200,000; and after the surface was dried, an absorbable iron-based alloy drug stent was made. A polylactic acid drug coating with a thickness of 12 to 16 um completely covered the tannic acid chemical conversion film and included 0.01 mg of sirolimus. The stent was implanted into an abdominal aorta of a rabbit and was then taken out after 3 months, and observation found that the stent was corroded to a certain extent and was subjected to full endothelialization, and no early thrombosis and inflammation phenomena were caused. Measurement was carried out with a radial supporting strength tester. Radial supporting strength test results of the stent and the complete corrosion cycle data monitored in the experiments of the same group of animals are specified in Table 1.

Contrast 1

A polished iron-based alloy coronary artery stent of the specification 30008 was selected, with its original radial strength of 175 kPa and weight of 5.5 mg, the surface of the stent was subjected to spray coating with a poly-dl-lactic acid-ethyl acetate solution with the molecular weight of 200,000, and after the surface was dried, an absorbable iron-based alloy stent was made. A polylactic acid coating with a thickness of 8 um completely covered the surface of the iron-based alloy stent. The stent was implanted into an abdominal aorta of a rabbit and was then taken out after 3 months, and observation found that the stent was corroded to a certain extent. Radial supporting strength test results of the stent and the complete corrosion cycle data monitored in the experiments of the same group of animals are specified in Table 1.

Contrast 2

A polished iron-based alloy coronary artery stent of the specification 30008 was selected, with its original radial strength of 145 kPa and weight of 4.5 mg, the surface of the stent was subjected to spray coating with a poly-dl-lactic acid-ethyl acetate solution with the molecular weight of 200,000, and after the surface was dried, an absorbable iron stent was made. A polylactic acid coating with a thickness of 12 um completely covered the surface of the iron stent. The stent was implanted into an abdominal aorta of a rabbit and was then taken out after 3 months, and observation found that the stent was severely corroded. Measurement was carried out with a radial supporting strength tester. Radial supporting strength test results of the stent and the complete corrosion cycle data monitored in the experiments of the same group of animals are specified in Table 1.

TABLE 1

Experimental Results of Embodiments 1 to 4 and Contrasts 1 to 2

| Embodiment | Stent Design | | | | | Radial Supporting | |
| --- | --- | --- | --- | --- | --- | --- | --- |
| | Original radial supporting strength/KPa | Wight of stent/mg | Thickness of conversion film/um | Thickness of polyester coating/um | Carried drug | StrengthPa after stent is implanted for 3 months/K | Corrosion Cycle/Month |
| Embodiment 1 | 145 | 4.5 | 0.4 to 0.5 | 6 | / | 100 | 24 |
| Embodiment 2 | 145 | 4.5 | 0.8 to 1.0 | 8 | / | 80 | 15 |
| Embodiment 3 | 145 | 4.5 | 1.6 to 1.8 | 12 | / | 80 | 12 |
| Embodiment 4 | 145 | 4.5 | 1.6 to 1.8 | 12 | sirolimus | 80 | 12 |
| Contrast 1 | 175 | 5.5 | 0 | 8 | / | 80 | 15 |
| Contrast 2 | 145 | 4.5 | 0 | 12 | / | <55 | 6 |

According to Table 1, compared with the radial supporting strength and the corrosion cycle in Contrast 2, the radial supporting strengths and the corrosion cycles of the stents provided by embodiments 1 to 4 all meet the design requirements after the stents are implanted for 3 months. When Embodiment 2 is compared with Contrast 1, by the arrangement of the tannic acid chemical conversion film between the iron-based alloy substrate and the polylactic acid coating, on the basis of ensuring that the stent has an ideal supporting strength after being implanted for 3 months, the stent has a decreased design size, and the amount of the iron-based alloy substrate is decreased, thus producing a decreased amount of stent corrosion products and making a complete absorption cycle shorter. When Embodiment 3 is compared with Contrast 2, under a condition of the same original specification of the stent, arrangement of the tannic acid chemical conversion film between the iron-based alloy substrate and the polylactic acid coating may delay corrosion of the iron-based alloy substrate in the initial stage of implantation (within 3 months), thus ensuring that the stent has a structural integrality and a high mechanical property in the initial stage of implantation.

The invention claimed is:

1. An absorbable iron-based alloy implanted medical device, comprising:
    an iron-based alloy substrate;
    a tannic acid chemical conversion film disposed on the surface of the iron-based alloy substrate, with the tannic acid chemical conversion film having a thickness of 0.4 to 0.5 um and covering 95 percent of the surface of the iron-based substrate; and
    a polylactic acid coating with a thickness of 6 um completely covering the tannic acid chemical conversion film.

2. The absorbable iron-based alloy implanted medical device according to claim 1, wherein the iron-based alloy substrate is an iron-based alloy or pure iron with a carbon content less than or equal to 2.11 weight percent.

3. The absorbable iron-based alloy implanted medical device according to claim 1, wherein the tannic acid chemical conversion film is a product generated by reaction of tannic acid and the iron-based alloy substrate.

4. The absorbable iron-based alloy implanted medical device according to claim 1, wherein the polylactic acid coating comprises an active drug which is an anti-intimal hyperplasia drug for treating vascular restenosis, an anticoagulant, an anti-platelet adhesion drug, an anti-infective drug, an antibacterial drug or an anti-tumor drug.

5. The absorbable iron-based alloy implanted medical device according to claim 1, wherein the implanted medical device is a heart implant, a blood vessel implant, a gynecological implant, an andrological implant, a respiratory implant or an orthopedic implant.

6. An absorbable iron-based alloy implanted medical device, comprising:
    an iron-based alloy substrate;
    a tannic acid chemical conversion film disposed on the surface of the iron-based alloy substrate, with the tannic acid chemical conversion film having a thickness of 0.8 to 1.0 um and completely covering the surface of the iron-based substrate; and
    a polylactic acid coating with a thickness of 8 um partially covering the tannic acid chemical conversion film.

7. The absorbable iron-based alloy implanted medical device according to claim 6, wherein the iron-based alloy substrate is an iron-based alloy or pure iron with a carbon content less than or equal to 2.11 weight percent.

8. The absorbable iron-based alloy implanted medical device according to claim 6, wherein the tannic acid chemical conversion film is a product generated by reaction of tannic acid and the iron-based alloy substrate.

9. The absorbable iron-based alloy implanted medical device according to claim 6, wherein the polylactic acid coating comprises an active drug which is an anti-intimal hyperplasia drug for treating vascular restenosis, an anticoagulant, an anti-platelet adhesion drug, an anti-infective drug, an antibacterial drug or an anti-tumor drug.

10. The absorbable iron-based alloy implanted medical device according to claim 6, wherein the implanted medical device is a heart implant, a blood vessel implant, a gynecological implant, an andrological implant, a respiratory implant or an orthopedic implant.

11. An absorbable iron-based alloy implanted medical device, comprising:
- an iron-based alloy substrate;
- a tannic acid chemical conversion film disposed on the surface of the iron-based alloy substrate, with the tannic acid chemical conversion film having a thickness of 1.6 to 1.8 um and completely covering the surface of the iron-based substrate; and
- a polylactic acid coating with a thickness of 12 um completely covering the tannic acid chemical conversion film.

12. The absorbable iron-based alloy implanted medical device according to claim 11, wherein the iron-based alloy substrate is an iron-based alloy or pure iron with a carbon content less than or equal to 2.11 weight percent.

13. The absorbable iron-based alloy implanted medical device according to claim 11, wherein the tannic acid chemical conversion film is a product generated by reaction of tannic acid and the iron-based alloy substrate.

14. The absorbable iron-based alloy implanted medical device according to claim 11, wherein the polylactic acid coating comprises an active drug which is an anti-intimal hyperplasia drug for treating vascular restenosis, an anticoagulant, an anti-platelet adhesion drug, an anti-infective drug, an antibacterial drug or an anti-tumor drug.

15. The absorbable iron-based alloy implanted medical device according to claim 11, wherein the implanted medical device is a heart implant, a blood vessel implant, a gynecological implant, an andrological implant, a respiratory implant or an orthopedic implant.

* * * * *